United States Patent
Willing et al.

(10) Patent No.: US 12,376,999 B2
(45) Date of Patent: Aug. 5, 2025

(54) ELASTIC DIAPER ELEMENT

(71) Applicant: RKW SE, Mannheim (DE)

(72) Inventors: Christoph Willing, Vreden (DE); Paul Waller, Rosenheim (DE); Michael Scherer, Flintsbach im Inn (DE); Reinhard Epping, Gronau-Epe (DE)

(73) Assignee: RKW SE, Mannheim (DE)

( * ) Notice: Subject to any disclaimer, the term of this patent is extended or adjusted under 35 U.S.C. 154(b) by 606 days.

(21) Appl. No.: 17/285,250

(22) PCT Filed: Jan. 22, 2020

(86) PCT No.: PCT/EP2020/051479
§ 371 (c)(1),
(2) Date: Apr. 14, 2021

(87) PCT Pub. No.: WO2020/169298
PCT Pub. Date: Aug. 27, 2020

(65) Prior Publication Data
US 2022/0117803 A1    Apr. 21, 2022

(30) Foreign Application Priority Data
Feb. 20, 2019 (DE) .......................... 102019104225.9

(51) Int. Cl.
*A61F 13/49* (2006.01)
*A61F 13/15* (2006.01)

(52) U.S. Cl.
CPC .... *A61F 13/4902* (2013.01); *A61F 13/15699* (2013.01); *A61F 13/49012* (2013.01); *A61F 2013/15983* (2013.01); *A61F 2013/49023* (2013.01)

(58) Field of Classification Search
CPC ............ A61F 13/4902; A61F 13/15699; A61F 13/49012; A61F 2013/15983; A61F 2013/49023; A61F 2013/51322; A61F 13/5116; A61F 2013/51165–51182
See application file for complete search history.

(56) References Cited

U.S. PATENT DOCUMENTS 5,576,090 A * 11/1996 Suzuki .............. A61F 13/15593
                                                            428/152
6,878,647 B1 * 4/2005 Rezai ................ A61F 13/49012
                                                            442/329
(Continued)

FOREIGN PATENT DOCUMENTS

EP        0182942        6/1986
EP        217032         2/1992
(Continued)

*Primary Examiner* — Susan S Su
*Assistant Examiner* — Erin A Kim
(74) *Attorney, Agent, or Firm* — Volpe Koenig

(57) ABSTRACT

An elastic diaper element that includes an elastic layer (1) and at least one layer (2) made of a nonwoven fabric. The element has connection portions (5) between the elastic layer (1) and the non-woven layer (2). The non-woven layer (2) is corrugated in the non-stretched state and has portions (6) that act as a reserve allowing stretching. The connection portions (5) include zones (8) in which there is a form-fitting bond of material of the layer (2) made of the nonwoven and solidified material of the elastic layer (1).

14 Claims, 1 Drawing Sheet

(56) References Cited

U.S. PATENT DOCUMENTS

| | | | | |
|---|---|---|---|---|
| 2004/0092903 A1* | 5/2004 | Olson | ............... | A61F 13/581 |
| | | | | 604/389 |
| 2005/0101216 A1* | 5/2005 | Middlesworth | ......... | A61F 13/51 |
| | | | | 28/155 |
| 2006/0083900 A1* | 4/2006 | Ashraf | ............... | B29C 55/08 |
| | | | | 156/163 |
| 2009/0159187 A1* | 6/2009 | Ashraf | ............... | B29C 55/20 |
| | | | | 156/163 |
| 2009/0254057 A1* | 10/2009 | Ceusters | ......... | A61F 13/49017 |
| | | | | 604/367 |
| 2009/0258210 A1* | 10/2009 | Iyad | ..................... | B32B 25/16 |
| | | | | 156/244.11 |
| 2009/0264844 A1* | 10/2009 | Autran | ............... | B32B 27/285 |
| | | | | 604/367 |
| 2014/0378924 A1* | 12/2014 | Turner | ............... | B32B 27/12 |
| | | | | 156/181 |
| 2018/0271716 A1* | 9/2018 | Dalal | ............... | A61F 13/49015 |
| 2018/0345641 A1* | 12/2018 | Angeli | ............... | B32B 5/022 |
| 2019/0254885 A1* | 8/2019 | Takeuchi | ......... | A61F 13/15739 |

FOREIGN PATENT DOCUMENTS

| | | |
|---|---|---|
| EP | 1740364 | 11/2005 |
| EP | 2024178 | 1/2013 |
| WO | 9534264 | 12/1995 |
| WO | 03075735 | 9/2004 |
| WO | 2006004637 | 1/2006 |
| WO | 2006044814 | 4/2006 |

\* cited by examiner

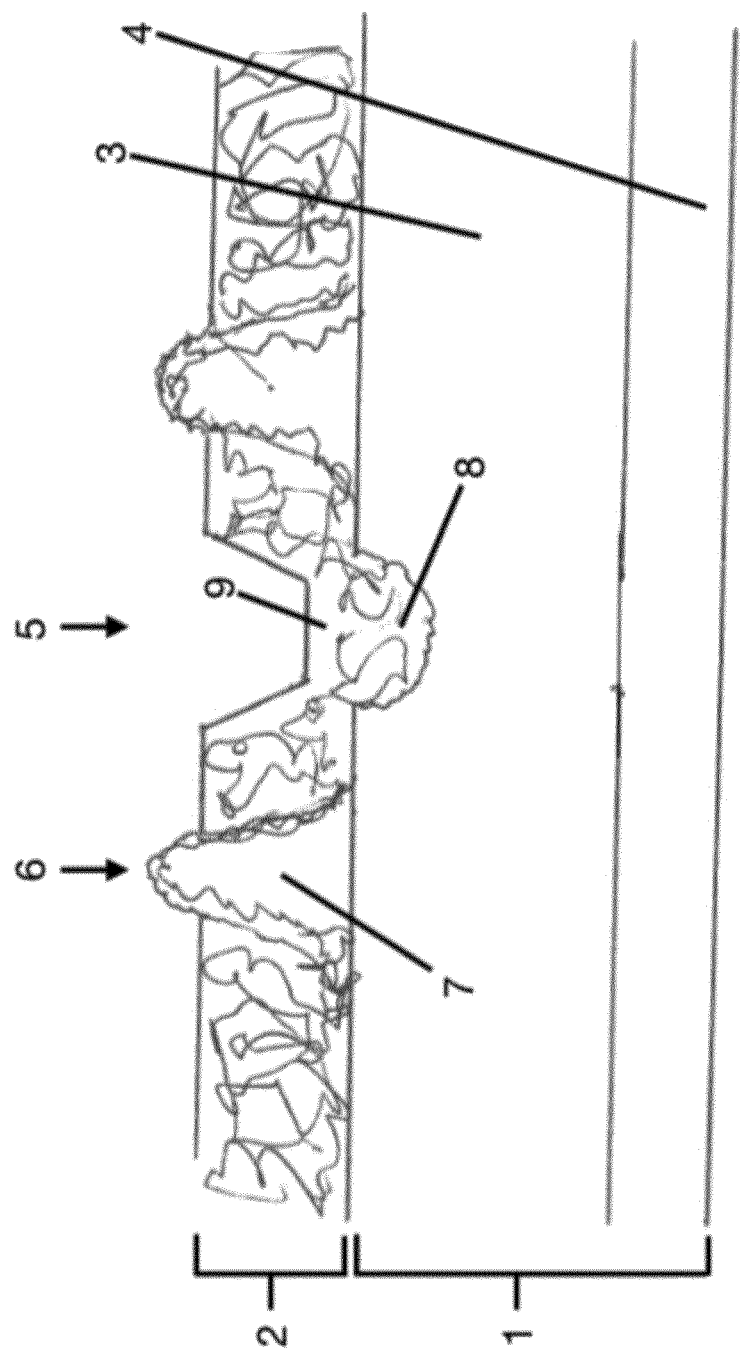

ELASTIC DIAPER ELEMENT

TECHNICAL FIELD AND DESCRIPTION

The invention relates to a stretchable diaper element with an elastic layer and at least one layer made of nonwoven, wherein the diaper element has connecting regions between the elastic layer and the layer made of nonwoven. The nonwoven layer comprises, in the non-stretched state of the diaper element, corrugated regions acting as a reserve for enabling stretching.

In the case of diapers, elastic elements are used in order to ensure good fit and tightness. The diaper element according to the invention is preferably used as a diaper waistband. The material is likewise particularly suitable for the use as an elastic closure element, a so-called back ear on baby diapers.

The diaper element according to the invention comprises a layer made of an elastic material. The elastic layer is provided on at least one side with a layer made of a nonwoven fabric. Such nonwoven fabrics generally have a limited extensibility. In the case of the diaper waistband elements according to the invention, a nonwoven layer is therefore connected in a corrugated form to the elastic layer. The troughs are connected to the elastic layer, whereas the crests project away from the elastic layer and enclose a cavity toward the elastic layer. As a result of the corrugations, the nonwoven layer in the non-stretched state forms a reserve for enabling stretching of the element.

BACKGROUND

Conventionally, such diaper elements are produced in that the elastic layer is first stretched and then the nonwoven layer is applied flatly to the elastic layer. The nonwoven layer is then connected in certain regions to the elastic layer by ultrasonic welding. After relaxation of the laminate, the nonwoven layer forms the desired corrugated structure.

A diaper with an upper and a lower layer is described in DE 689 23 866 T2. An elastic band is fastened to the elastic layer in the non-loaded state. The elastic band is connected to the elastic layer over the whole area. After stretching and relaxation of the elastic band, shirred regions are formed.

EP 217032 B1 relates to a laminate with an elastic material which, at points which are spaced apart from one another, is connected to at least one web which is to be laid in pleats. The elastic material is a non-corrugated, elastic fiber web.

A method for producing a corrugated stretch laminate is described in EP 1 807 035 B1. In this case, an elastic composition is applied in a molten state to a carrier web to form an elastic element. A stretch composite preform is formed by stretching the carrier web. The preform is then stretched. A substrate is connected to the stretched preform in order to form a corrugated stretch laminate upon relaxation of the stretched preform.

EP 2 024 178 B1 describes a method for producing an elastically stretchable laminate with three layers. The laminate comprises an elastic film and two layers made of non-elastic nonwoven fabric. In one variant, a nonwoven crepe fabric is used. A first elastic laminate is connected to a non-elastic nonwoven layer in a stretched state.

SUMMARY

It is an object of the present invention to provide a diaper element which has favorable stretching properties and at the same time ensures high tear resistance. In the case of force loading, the element is intended to behave in a stretchable manner, but also to build up sufficient resistance, which provides the consumer with the feeling of a high-quality product. In the use as a "back ear", the element must not tear since otherwise the diaper can no longer be closed. In this case, by way of a corrugated design, at least one nonwoven layer is intended to provide a sufficient but not excessive reserve for stretching of the element. The laminate is intended to pose no risk to health and be environmentally sustainable. In addition, the intention is for no odors to emanate from the product. Furthermore, the element is intended to have pleasant haptics. The diaper element is also intended to ensure optimum fit of the diaper on the body, such that cavities between the diaper and the body are avoided and leakage of liquid is prevented.

This object is achieved according to the invention by way of a diaper element, a method and the use including one or more of the features described herein. Preferred variants can be gathered from the claims, the description, the exemplary embodiment and the drawing.

According to the invention, the connecting regions between the corrugated nonwoven layer and the elastic layer are formed by way of a form-fitting bond, in which nonwoven material is present in the solidified material of the elastic layer. In contrast to conventional waistband laminates, in order to produce the laminates according to the invention, an apparatus is first used to form a corrugated structure from a smooth nonwoven layer by deformation of the surface. As a result, indentations and elevations are formed, that is to say crests and troughs. An elastic layer is then extruded onto the corrugated nonwoven layer. The indentations of the nonwoven layer are pushed into the molten elastic layer in a targeted manner. After solidification of the elastic layer, form-fitting connecting regions are formed, in which nonwoven material is present in the solidified elastic material. The elevations of the nonwoven layer project away from the elastic layer and form a stretch reserve. In the region of the stretch reserve, cavities are enclosed between the nonwoven layer and the elastic layer.

In contrast to conventional methods, during the formation of the laminate, the elastic layer is not in the form of a film but rather in molten form and is not stretched prior to the connecting step. Furthermore, during the connecting step, the nonwoven layer is not applied to the elastic layer in flat form, but rather in corrugated form.

During the connecting operation, there is no action of heat from the outside, as would be the case for example when ultrasonic welding is employed. In the case of the laminate according to the invention, the corrugated nonwoven material is thus subjected to no thermal loading from the outside. As a result, pinholing of the film, as may occur in the case of conventional connecting methods, for example in the case of ultrasonic welding, is for example avoided. No adhesives are required for producing the laminate. Compression is not effected over the total area.

The invention is described in more detail below.

Analogously to the expression "corrugated", the expressions "grooved", "pleated", "shirred", "crimped", "ribbed", "folded" or "creped" can also be used and describe the spatial alignment of the nonwoven fabric. According to the invention, the corrugated configuration of the nonwoven layer is obtained in that, prior to the connecting process, the nonwoven fabric is guided via a special apparatus, for example a ribbed guide element, a finger strip, a ribbed roll or a ridged roll.

In one variant of the invention, the corrugated profile of the nonwoven layer can be formed between two rolls which have elevations and indentations, wherein at least one of the two rolls is configured in the form of a ridged roll. The elevations of the one roll in this case engage in the indentations of the other roll, and vice versa.

In an alternative variant of the invention, the corrugated profile of the nonwoven layer is formed between a roll and a further element which, like the roll, also has elevations and indentations. The elevations of the roll in this case engage in the indentations of the element, and vice versa. The element extends in an arcuate manner as far as the extruded elastic layer, such that the corrugated profile of the nonwoven layer remains unchanged up to the connecting step.

The expression "nonwoven" relates to a substance which can be produced from continuous filaments and/or discontinuous fibers, without weaving or knitting, by processes such as spunbonding, carding or melt-blowing. The nonwoven fabric can comprise one or more layers of nonwoven, wherein each layer can contain continuous filaments or discontinuous fibers. Nonwoven can also comprise bicomponent fibers which can have fiber structures such as for example shell-core or side-by-side.

The expression "elastic" preferably relates to any material that, upon application of a directed force, is able to stretch to a stretched length of at least approximately 160% of its relaxed, original length without tearing or breaking and that, when the applied force is canceled, returns by at least approximately 55% of its extension, preferably substantially to its original length, that is to say the returned length is less than approximately 120%, preferably less than approximately 110%, more preferably less than approximately 105%, of the relaxed original length.

The expression "diaper" preferably relates to disposable absorption articles which absorb and trap fluids. The term encompasses, inter alia, diapers with closures, diaper pants, training pants, swim diapers, incontinence articles for adults and the like.

In the production of the diaper element, prior to the connecting step, the nonwoven layer is brought into a three-dimensional, corrugated shape by being guided via a special apparatus. This apparatus may be a roll which has elevations and, as a result, forms the corrugated profile of the nonwoven layer. In addition or as an alternative, prior to the connecting step, the nonwoven layer can be guided via an element which extends in an arcuate manner as far as the extruded elastic layer, such that the corrugated profile of the nonwoven layer remains unchanged up to the connecting step. The element may for example be configured in the form of a finger strip.

Besides the melting capacity of the extruder, the production of the laminate requires no energy from the outside, as would be the case for example in the event of ultrasonic welding. The melt solidifies and the connecting regions according to the invention form. The connecting regions are thus provided in such a way that the nonwoven layer is subjected to no thermal loading from the outside, as would be the case for example in the event of ultrasonic welding or melting of the elastic layer by means of heated rolls.

As a result of the selective heating of the elastic layer by cast extrusion with simultaneous generation of a flow of heat from the inside to the outside during the connecting step, the load-bearing structure of the elastic layer remains unchanged. By ensuring a flow of heat from the inside to the outside during the connecting operation, a laminate is provided which has particularly favorable properties as a diaper waistband.

The flow of heat from the inside to the outside can be controlled in a targeted manner. In a particularly favorable embodiment of the invention, use is made of at least one chill roll for this purpose. As a result of a decrease in the surface temperature of the chill roll, it is possible for the flow of the heat energy flowing from the inside to the outside to be increased.

The elastic layer is preferably in molten form after extrusion above a temperature of 180° C. Cooling by more than 80° C., preferably by more than 130° C., is preferably performed during the connecting step.

The connecting regions according to the invention are preferably configured in a strip-like manner in rows which are arranged next to one another. There is preferably a straight profile within a row. The alignment of the connecting regions is preferably perpendicular to the tensile direction of the diaper element, such that the individual rows are aligned transverse to the tensile direction of the diaper waistband.

The ratio of the elevated regions to the sunken regions of the apparatuses, which are used for forming the corrugated profile and during the connecting step, is important for an optimal diaper waistband laminate. This ratio is also referred to as the web-to-groove ratio. This web-to-groove ratio is preferably less than 1:1, preferably less than 1:2.

It has proven to be particularly expedient for the connecting regions to have a width of more than 0.1 mm, preferably more than 0.3 mm, in particular of more than 0.5 mm and/or a width of less than 1.5 mm, preferably less than 1.3 mm, in particular less than 0.9 mm.

In a preferred variant of the invention, the connecting regions have external zones in which no elastic material has penetrated. There is no form-fitting bond in the external zones of the connecting regions since these zones are free of elastic material. The external zones prevent a situation whereby elastic material pierces through the nonwoven layer.

There is a form-fitting bond of solidified elastic material and nonwoven material in the inner zones of the connecting regions. In this case, the nonwoven material is also preferably not incipiently melted in the inner zones, but rather the fibers are merely pushed into the elastic melt. The material of the elastic layer surrounds the filaments of the nonwoven layer, such that a form-fitting bond is produced in the inner zone of the connecting regions after solidification of the elastic layer.

In individual cases, it may also be the case that at least individual fibers of the nonwoven material are incipiently melted in the inner zone. It is also possible from a purely theoretical standpoint that, in the inner zone, the nonwoven material is in completely melted form in the elastic melt.

In all cases, after solidification of the elastic material, there is a form-fitting bond of nonwoven material and solidified material of the elastic layer in the inner zone.

Arranged between the connecting regions are regions in which the elevations of the corrugated nonwoven layer project away from the elastic layer in corrugated form and enclose cavities. These regions serve as reserve for the stretching of the diaper element, there being no connection between the nonwoven layer and the elastic layer in these regions.

With regard to the total area of the flat film, the reserve regions comprise a significantly greater proportion than the connecting regions. The proportion of the reserve regions is preferably more than 60%, in particular more than 70%, preferably more than 80%, of the total area. As total area, the surface of the solidified flat elastic layer is used as reference.

There is no connection of the nonwoven layer to the elastic layer in the reserve regions.

As a result of the corrugated design, the nonwoven layer of a laminate portion is significantly longer than the elastic layer. The nonwoven layer is preferably longer than the elastic layer by more than a factor of 1.5, in particular by more than a factor of 2.0, preferably by more than a factor of 2.5.

In a preferred variant of the invention, after the connecting operation, the laminate is stretched in a transverse direction. The stretching is preferably performed below the elongation at break of the nonwoven layer.

It has proven to be particularly expedient for the non-bonding regions, that is to say the reserve regions, to have a width of more than 1.5 mm, preferably more than 2 mm, in particular more than 2.5 mm and/or a width of less than 6 mm, preferably less than 5 mm, in particular less than 4 mm.

The bonding regions preferably have a width of more than 0.1 mm, in particular more than 0.2 mm, preferably more than 0.3 mm and/or a width of less than 1 mm, preferably less than 0.8 mm, preferably less than 0.6 mm.

The reserve regions or connecting regions are preferably configured in a strip-like manner transverse to the tensile direction of the diaper waistband.

In order to create the connecting regions, use is preferably made of rolls having a surface structure, wherein the height of the elevations is more than 100 μm, preferably more than 500 μm, in particular more than 1 mm and/or less than 8 mm, preferably less than 10 mm, in particular less than 12 mm.

The nonwoven layer is preferably composed of a hydroentangled nonwoven fabric. Hydroentanglement makes it possible to reorient the fibers in the nonwoven fabric, and therefore the original two-dimensional fiber alignment is transferred into a three-dimensional fiber orientation. The fibers are incorporated in the nonwoven to a more pronounced extent. This nonwoven layer preferably has a specific weight of 5 to 80 g/m$^2$, preferably of 10 to 70 g/m$^2$, in particular of 15 to 35 g/m$^2$.

The hydroentangled nonwoven fabric layer preferably involves nonwoven fabrics made of continuous filaments. On account of their production process, these fabrics provide a fibrous web which is preferably of loop-like configuration.

Spinnable polymers such as for example polyester, PLA, polyolefins, in particular polypropylene and polyethylene, can be used as material for producing the continuous filaments.

Particularly advantageous is the use according to the invention of hydroentangled nonwoven fabric as the corrugated nonwoven layer which forms reserve regions for stretching of the diaper element. As a result of the formation of corrugations, the hydroentangled nonwoven fabric deforms in such a way that the fibers in the connecting regions are stretched and, as a result, preferably undergo orientation. As a result, particularly advantageous connecting zones are provided, in which the molten material surrounds the stretched and aligned filaments of the hydroentangled nonwoven fabric and, after solidification, a particularly favorable form-fitting bond is produced. It has been determined, surprisingly, that a diaper element with particularly favorable properties is provided when a hydroentangled nonwoven fabric is used. The nonwoven layer made of the hydroentangled nonwoven fabric can be deformed in a particularly satisfactory manner. The nonwoven web supplied loses virtually no width during the production process in spite of the formation of corrugations.

The elastic layer preferably involves a polypropylene and/or polyethylene block copolymer. The elastic film preferably has a specific weight of 5 to 140 g/m$^2$, in particular of 10 to 130 g/m$^2$, preferably of 20 to 40 g/m$^2$.

As an alternative, the elastic layer can also be composed of an SBC (styrene block copolymer) or an elastic polyurethane.

In one variant of the invention, the elastic layer is of multi-layered construction and is preferably embodied as a co-extruded film. In an advantageous variant, said film comprises a "core layer" and a "skin layer" which is significantly thinner compared with said core layer. The skin layer preferably has a specific weight of less than 5 g/m$^2$, in particular less than 4 g/m$^2$, preferably less than 3 g/m$^2$ and/or more than 0.3 g/m$^2$, in particular more than 0.6 g/m$^2$, preferably more than 0.9 g/m$^2$.

In one variant, the core layer is embedded between two skin-layer outer layers.

The core layer is preferably composed of an elastic polyolefin or an SBC (styrene block copolymer) or a polyurethane.

The skin layer is preferably composed of a polyethylene, a polypropylene or an EVA (ethylene-vinyl acetate copolymer).

In an expedient variant of the invention, filled polyolefins are used as skin layer. Examples of fillers used are mineral materials such as calcium carbonate or talc. The filler proportion is preferably more than 60% by weight, in particular more than 70% by weight, preferably more than 80% by weight.

Blends can also be used to form the skin layer. In this case, blends of polyolefins with polystyrene and/or blends of polyolefins with PLA are suitable, for example. No filler is required in the case of such blends.

The skin layer is designed such that it ensures deblocking from the tacky core layer. In addition, the skin layer can be easily deformed and can be readily stretched.

In one variant of the invention, the diaper element comprises a nonwoven layer made of a carded nonwoven fabric. The carded nonwoven fabric used is preferably composed of polypropylene fibers and/or of mixtures of different fiber types, such as, for example, of polypropylene/viscose, polypropylene/polyamide, polypropylene/polyester, etc. The carded nonwoven fabric can also be composed of polypropylene and/or polyethylene copolymer. The specific weight per unit area of the carded nonwoven fabric is preferably 10 to 40 g/m$^2$, in particular between 15 to 25 g/m$^2$. The carded nonwoven fabric can be consolidated for example by a calender and/or by means of the action of air and/or water jet.

In the case of the diaper element, the elastic layer can also be embedded between two layers made of nonwoven. In this case, at least one layer is preferably composed of a hydroentangled nonwoven material. The second nonwoven layer can also be composed either of a hydroentangled nonwoven fabric or a carded nonwoven fabric or a spunbonded nonwoven fabric. The second nonwoven layer can also either be of corrugated form or have a flat profile.

By way of the design of the diaper element according to the invention, the diaper bears against the body in optimum fashion and ensures optimum fit. As a result of the height of its fold arrangement, the diaper element has a voluminous design and fills cavities between the diaper and the body, such that a leak is effectively prevented.

BRIEF DESCRIPTION OF THE DRAWINGS

Further advantages and features of the invention emerge from the description of an exemplary embodiment with reference to a drawing and from the drawing itself.

The sole Figure shows a section through a diaper element according to the invention.

DETAILED DESCRIPTION

The figure shows a section through a diaper element according to the invention. The laminate comprises an elastic layer 1 and a nonwoven layer 2 made of a corrugated nonwoven fabric. This nonwoven fabric is a hydroentangled nonwoven fabric, a spunbonded nonwoven made of continuous filaments being used in the exemplary embodiment. According to the invention, the nonwoven fabric is brought into a corrugated form prior to the connection to the elastic layer 1. After the elastic layer 1 has been extruded onto the corrugated nonwoven layer 2, the indentations of the nonwoven fabric are pushed into the molten elastic layer 1, such that connecting regions 5 form between the corrugated nonwoven fabric 2 and the elastic layer 1.

In the exemplary embodiment, the elastic layer 1 is embodied as a multi-layered co-extruded film, having a core layer 3 and a further layer 4 which is configured in the form of a "skin layer". The ratio of the thickness of the core layer 3 to the further layer 4 is preferably more than 8:1, in particular more than 10:1, in particular more than 12:1. The skin layer 4 preferably has a weight between 1 to 3 g/m².

The core layer 3 is preferably composed of thermoplastic polymers. In this case, preference is given to using polypropylene-polyethylene block copolymers, for example of the Exxon Vistamaxx (PP-based) product series: VM 6102 or VM 6202 or VM 7810 and/or of the Dow Infuse (PE-based) product series: Infuse 9507, Infuse 9107.

The outer layer 4 is preferably composed of a polyolefin or an ethylene-vinyl acetate copolymer (EVA). The outer layer 4, in contrast to the core layer 3, is not "tacky" and thus prevents undesired adhesion.

According to the invention, the laminate comprises connecting regions 5 and reserve regions 6. The reserve regions 6 exhibit no, or only a very weak, bond to the elastic layer 1 and preferably enclose cavities 7.

In the exemplary embodiment, the web-to-groove ratio of the roll which brings the nonwoven into a corrugated form and pushes the indentations of the corrugated nonwoven layer 2 into the molten elastic layer 1 is 1:6, past the web width is preferably 0.5 mm and the groove width is preferably 3 mm.

In the exemplary embodiment, the connecting regions 5 according to the invention have different zones 8, 9.

The external zone 9 is free of elastic material, such that the elastic material does not pierce through the nonwoven layer 2. The nonwoven material in the external zone 8 is not thermally influenced from the outside, such that the filaments of the layer 2 made of nonwoven are not incipiently melted.

There is a form-fitting bond of solidified elastic material and nonwoven material in the inner zone 8 of the connecting regions 5. In the exemplary embodiment, the nonwoven material is also not incipiently melted in the inner zone 8 in this case. The continuous filaments of the hydroentangled nonwoven fabric are merely pushed into the elastic melt, such that a form-fitting bond is produced after solidification. In this case, during the connecting process, the continuous filaments of the hydroentangled nonwoven fabric themselves remain largely uninfluenced. They are merely surrounded by the molten material of the elastic layer 1.

After solidification of the elastic material, there is a form-fitting bond of nonwoven material and solidified material of the elastic layer 1 in the inner zone 8.

The laminate illustrated in the figure is connected together between a pair of rolls, in the case of which, looking at the drawing, a profiled roll with elevations pushes the nonwoven layer 2 into the elastic layer 1 from above and, from below, there is arranged a mating roll with a smooth surface. In the production of the laminate illustrated in the figure, a chill roll is used as mating roll. The chill roll is a steel roll. The roll which acts from above is a non-cooled roll.

The rolls used for connection are driven at a spacing, wherein a fixed spacing is set.

The laminate preferably has a specific weight per unit area of more than 10 g/m², in particular more than 20 g/m², preferably more than 30 g/m² and/or less than 200 g/m², in particular less than 150 g/m², preferably less than 100 g/m².

In the exemplary embodiment, the connecting regions 5 and the reserve regions 6 are of strip-like design, wherein the strips run transversely with respect to the tensile direction of the diaper element.

The strips of the connecting regions 5 have a width of between 0.1 and 1 mm. In the exemplary embodiment, the connecting regions 5 have a width of 0.5 mm.

The strips of the reserve regions 6, in which there is no connection between the nonwoven layer 2 and the elastic layer 1, have a width of between 2 and 6 mm.

In the exemplary embodiment, the reserve regions 6 have a width of 3 mm. In the exemplary embodiment, the connecting regions 5 thus have a proportion of 0.5/3.5=14.3%, and the reserve regions 6 have a proportion of 3/3.5=85.7%, in relation to the surface of the flat, non-stretched elastic layer 1.

The invention claimed is:

1. A stretchable diaper element, comprising
   an extruded elastic layer (1);
   a layer (2) made of nonwoven material;
   the elastic layer has spaced-apart connecting regions (5) between the elastic layer (1) and the layer (2) made of the nonwoven material;
   the layer (2) made of the nonwoven material is corrugated in a non-stretched state of the diaper element to form regions (6) acting as reserve that are configured to enable stretching;
   the connecting regions (5) comprise zones (8) in which there is a form-fitting bond of material of the layer (2) made of the nonwoven material, including fibers of the nonwoven material that are not melted that are pressed into and pierce through a surface of the extruded elastic layer (1) when the extruded elastic layer (1) is in a molten state, and the fibers of the nonwoven material are held in place by a form-fitting bond with the extruded elastic layer (2) after solidification; and
   the fibers of the layer (2) made of the nonwoven material are in at least one of oriented or stretched form in the connecting regions (5).

2. The diaper element as claimed in claim 1, wherein the connecting regions (5) have outer zones (9) in which no material of the elastic layer (1) has penetrated, such that the elastic layer (1) does not pierce through the layer (2) made of the nonwoven material.

3. The diaper element as claimed in claim 2, wherein there is no incipient melting of the nonwoven material in the outer zones (9).

4. The diaper element as claimed in claim 1, wherein there is no incipient melting of the nonwoven material in the zones (8) in which there is a form-fitting bond of the nonwoven material and solidified elastic material.

5. The diaper element as claimed in claim 1, wherein the layer (2) made of the nonwoven material is composed of a hydroentangled nonwoven fabric, and the nonwoven fabric has a specific weight of 10 to 70 g/m².

6. The diaper element as claimed in claim 1, wherein the elastic layer (1) is a multi-layered construction and includes a core layer (3) and at least one further layer (4).

7. The diaper element as claimed in claim 1, further comprising a further layer made of nonwoven, and the elastic layer (1) is arranged between the two layers made of nonwoven.

8. A method for producing a laminate for a stretchable diaper element, comprising the following steps:
   forming a corrugated layer (2) made of nonwoven material with elevations and indentations,
   extruding an elastic layer (1),
   impressing the elevations or indentations of the corrugated nonwoven material layer (2) into the elastic layer (1) while the elastic layer is molten,
   forming spaced-apart connecting regions (5) between the layer (2) made of the nonwoven material and the elastic layer (1) by fibers of the nonwoven material that are not melted being pressed into and piercing through a surface of the elastic layer (1) when the elastic layer (1) is molten, and the fibers of the nonwoven material being held in place by a form-fitting bond with the extruded elastic layer (2) after solidification, and
   at least one of orienting or stretching the fibers of the layer (2) made of the nonwoven in the connecting regions (5).

9. The method as claimed in claim 8, further comprising, after solidification of the material of the elastic layer (1), stretching the laminate in a transverse direction.

10. The method of claim 8, further comprising incorporating the laminate as a stretchable diaper element.

11. The method of claim 10, wherein the stretchable diaper element is a diaper waistband.

12. The diaper element as claimed in claim 5, wherein the layer (2) made of the nonwoven material is composed of the hydroentangled nonwoven fabric which is made of made of continuous filaments.

13. The diaper element as claimed in claim 1, wherein the elastic film has a specific weight of 10 to 130 g/m².

14. The diaper element as claimed in claim 13, wherein the layer (2) made of the nonwoven material is composed of a hydroentangled nonwoven fabric, and the nonwoven fabric has a specific weight of 10 to 70 g/m².

* * * * *